(12) United States Patent
Hayashi et al.

(10) Patent No.: US 7,041,994 B2
(45) Date of Patent: May 9, 2006

(54) RADIOPROTECTIVE MATERIALS AND UTILIZATION THEREOF

(75) Inventors: Toshio Hayashi, Sakai (JP); Masakazu Furuta, Osaka (JP); Akihito Tsuchiya, Shiga (JP)

(73) Assignee: Allmighty Co., Ltd., Hyogo (JP)

( * ) Notice: Subject to any disclaimer, the term of this patent is extended or adjusted under 35 U.S.C. 154(b) by 337 days.

(21) Appl. No.: 10/149,333

(22) PCT Filed: Dec. 8, 2000

(86) PCT No.: PCT/JP00/08726

§ 371 (c)(1),
(2), (4) Date: Jun. 6, 2002

(87) PCT Pub. No.: WO01/43143

PCT Pub. Date: Jun. 14, 2001

(65) Prior Publication Data

US 2003/0080303 A1   May 1, 2003

(30) Foreign Application Priority Data

Dec. 8, 1999   (JP) ................................ 11-349438

(51) Int. Cl.
*G21F 1/00* (2006.01)

(52) U.S. Cl. .................... 250/515.1; 430/270; 524/401
(58) Field of Classification Search ............. 250/515.1; 430/270; 524/401
See application file for complete search history.

(56) References Cited

U.S. PATENT DOCUMENTS

| | | | | |
|---|---|---|---|---|
| 3,670,025 A | * | 6/1972 | Susi et al. | 564/309 |
| 5,108,873 A | * | 4/1992 | Fukui et al. | 430/270.19 |
| 5,204,099 A | | 4/1993 | Barbier et al. | |
| 2004/0147652 A1 | * | 7/2004 | Lemer et al. | 524/401 |

FOREIGN PATENT DOCUMENTS

| | | |
|---|---|---|
| EP | 0 379 409 A1 | 7/1990 |
| JP | 56-65865 | 6/1981 |
| JP | 01 146815 A | 6/1989 |
| JP | 09-255525 | 9/1997 |
| JP | 09-255776 | 9/1997 |
| JP | 09-255936 | 9/1997 |
| JP | 09-255937 | 9/1997 |

OTHER PUBLICATIONS

Supplementary European Search Report from corresponding European Patent Application Serial No. EP 00 98 0024.

* cited by examiner

*Primary Examiner*—Nikita Wells
*Assistant Examiner*—Zia R. Hashmi
(74) *Attorney, Agent, or Firm*—Knobbe, Martens, Olson & Bear, L.L.P.

(57) ABSTRACT

The present invention provides radioprotective materials and products produced using the materials, the materials and products being easily usable for blocking effects of radiations, exposure to which occurs unconsciously in daily life or in a working environment. Specifically stated, the present invention provides radioprotective materials containing polyamino acid(s) or derivative(s) thereof; the radioprotective materials in which the polyamino acid(s) comprises at least one amino acid selected from the group consisting of glutamic acid, phenylalanine, alanine and leucine; and the radioprotective materials in which the polyamino acid(s) or derivative(s) thereof is modified with sugar component(s). The present invention further provides radioprotective products produced using the radioprotective materials.

9 Claims, 8 Drawing Sheets

RADIOPROTECTIVE MATERIALS AND UTILIZATION THEREOF

This application is the U.S. National Phase under 35 U.S.C. §371 of International Application PCT/JP00/08726, filed Dec. 8, 2000, which claims priority to Japanese Patent Application No. 11/349438, filed Dec. 8, 1999. The International Application was not published under PCT Article 21(2) in English.

TECHNICAL FIELD

The present invention relates to materials capable of reducing adverse effects of radiations, i.e., radioprotective materials. The present invention further relates to methods for radioprotection using the radioprotective materials, and products having radioprotective effects owing to the radioprotective materials contained therein.

BACKGROUND ART

In recent years, increasing amounts of radioactive waste are generated from nuclear power facilities such as nuclear power plants, and medical facilities, universities and laboratories that use radioisotopes. Accordingly, a reliable measure for radioprotection is demanded.

Further, it is said that miners in mines of uranium ore, coal or metals are exposed to more than 6 times as much radiation from the earth's crust as allowed by international recommendations for radiation workers. Moreover, the amount of radiation from outer space (cosmic rays) to which flight crews are said to be exposed is much greater than that to which miners are exposed. A solution of these problems is urgently required.

Besides these specific facilities, luminous paints on clock or watch faces, glow lamps in fluorescent lamp devices, discharge tubes in displays in gas stations or the like, and smoke detectors in buildings employ isotopes that emit alpha rays or beta rays. Therefore, proper radiation control is always necessary in production sites of these items.

"Radiations", in a broad sense, include cosmic rays, radio waves, infrared radiation, visible light, Ultraviolet-A, Ultraviolet-B, Ultraviolet-C, directly ionizing alpha rays, beta rays, proton beams and baryon beams, indirectly ionizing X rays, gamma rays, electron beams and neutron beams, etc.

Among these radiations, Ultraviolet-A, Ultraviolet-B, directly ionizing alpha rays, beta rays, proton beams and baryon beams and indirectly ionizing X rays, gamma rays, electron beams and neutron beams necessitate radioprotection.

For protecting the internal or external (such as the skin, hair, eyes or the like) parts of the body from ultraviolet rays, sunglasses with large, light-colored lens, hats with all-around brims with a width of at least 7 cm, dark-colored clothes made of polyester fibers or hemp fibers, ultraviolet blocking cosmetics containing titanium oxide are reportedly effective. However, these means block only Ultraviolet-B, which, for instance, damages DNA in the epidermis of the body, promotes the formation of melanin pigment, rapidly increases active oxygen and thereby ages the tissue cells of the epidermis, and causes skin spots. On the other hand, Ultraviolet-C reaching the earth has been greatly increasing in recent years owing to the destruction of the ozone layer, and thus the effects of Ultraviolet-C pose problems. Further, it is known that Ultraviolet-A penetrates deep into the dermis of the body and cuts or destroys elastic fibers to thereby form unremovable wrinkles or cause cataracts. Thus, protection means against these ultraviolet rays are also hoped for.

Moreover, exposure to alpha rays, beta rays, X rays, gamma rays or like ionizing radiation which permeates the human body not only causes acute disorders of the body, including those of the blood and organs, but also has long-term averse effects on the human body, such as carcinogenesis, genetic damage or the like. Development of a protective material against these radiations is desired, in order to ensure radioprotection for people in general, as well as people who work with radiation and nuclear power.

DISCLOSURE OF THE INVENTION

An object of the present invention is to provide a radioprotective material easily usable for blocking adverse effects of radiations, exposure to which occurs or is likely to occur inevitably, unconsciously or accidentally in daily life or in a working environment, and for affording protection from exposure to such radiations. Another object of the invention is to provide radioprotective products produced using the radioprotective material. A further object of the invention is to provide a method using the radioprotective material to prevent exposure to radiations.

The present inventors carried out extensive research to achieve the above objects. As a result, the inventors found that polyamino acids and their derivatives are capable of significantly blocking or reducing adverse effects of various radiations, and confirmed that use of this characteristic of polyamino acids or their derivatives makes it possible to protect organisms or articles from inevitable or unconscious radiation exposure in daily life or in a working environment. The present invention has been accomplished based on these findings.

The present invention provides the following:

1. A radioprotective material comprising a polyamino acid or acids or a derivative or derivatives thereof.

2. A radioprotective material according to item 1, wherein the polyamino acid or acids comprise a water-soluble amino acid or acids or a water-soluble derivative or derivatives thereof.

3. A radioprotective material according to item 1, wherein the polyamino acid or acids comprise at least one amino acid selected from the group consisting of glutamic acid, phenylalanine, alanine and leucine.

4. A radioprotective material according to item 1, wherein the polyamino acid or acids or derivative or derivatives thereof are modified with a sugar component or components.

5. A radioprotective material according to item 4, wherein the sugar component or components are at least one member selected from the group consisting of monosaccharides and oligosaccharides.

6. A radioprotective material according to item 1, which provides protection from at least one member selected from the group consisting of gamma rays, X rays, beta rays, ultraviolet rays, alpha rays, cosmic rays, electron beams and baryon beams.

7. A radioprotective product comprising a radioprotective material according to item 1.

8. A radioprotective product according to item 7, which is at least one member selected from the group consisting of radioprotective films, radioprotective sheets, radioprotective coating agents, radioprotective cosmetic products, radioprotective fiber products, radioprotective preparations and radiation-resistant medical materials.

9. Use of a polyamino acid or acids or a derivative or derivatives thereof for production of a radioprotective material.

10. Use of a polyamino acid or acids or a derivative or derivatives thereof for production of a radioprotective product.

11. A method for blocking or reducing adverse effects of radiations on an object, the method using a radioprotective material according to item 1.

12. A method according to item 11, wherein the radioprotective material according to item 1 is mixed with, placed over, or immobilized on the object.

13. A method for blocking or reducing adverse effects of radiations on an object, the method using a radioprotective product according to item 7.

14. A method according to item 13, wherein the radioprotective material according to item 7 is administered to (ingested by), placed over (covered, coated or mounted on) or applied to the object.

Since the radioprotective material of the invention is capable of blocking or reducing the effects of radiations, the material can significantly prevent possible radiation exposure in nuclear power facilities, medical facilities, aircrafts in flight, uranium ore refineries, construction sites using radiography, etc. In addition, the material of the invention can protect organisms or articles such as precision equipment, photographic dry plates or the like, from damages caused by radiations from experimental equipment, color televisions or like electric appliances containing radiation tubes, or by radiations from outer space or the earth's crust. Moreover, since the material of the invention is biodegradable into nontoxic substances, it is also valuable from an environmental conservation point of view.

In this specification and the appended claims, the term "radiation" is used in its broad sense. Specifically stated, radiations include cosmic rays, radio waves, electromagnetic waves, infrared radiation, visible light, Ultraviolet-A, Ultraviolet-B, Ultraviolet-C, directly ionizing radiations such as alpha rays, beta rays, proton beams and baryon beams, indirectly ionizing radiations such as X rays, gamma rays, electron beams and neutron beams, and the like. Preferably, the radiations in the present invention are those against which protection is required, such as electromagnetic waves, Ultraviolet-A, Ultraviolet-B, directly ionizing radiations such as alpha rays, beta rays and proton beams, and indirectly ionizing radiations such as X rays, gamma rays and neutron beams.

BEST MODE FOR CARRYING OUT THE INVENTION

The radioprotective material of the invention comprises a polyamino acid or acids.

Polyamino acids usable in the invention include poly-α-amino acids obtained mainly by synthesis, and poly-γ-amino acids, poly-ε-amino acids and poly-δ-amino acids, which are mainly naturally occurring.

The polyamino acid for use in the invention may be either natural or synthetic. Usually, synthetic polyamino acids are relatively high molecular α-amino acid condensates obtained by a one-step condensation (polymerization) reaction carried out using an α-amino acid or a derivative thereof as a monomer. The α-amino acid condensates are usually solid and biodegradable, and therefore are preferable from an environmental conservation point of view. Further, some of the α-amino acid condensates are known to be permeable to oxygen and water. It is also known that poly-α-amino acids have abrasion resistance. Moreover, synthetic polyamino acids are polymers whose main chain structure is formed by completely the same peptide bonds as those of natural proteins, and have high compatibility with living tissues, non-antigenicity, biodegradability and other properties. Thus, synthetic polyamino acids are suitable as radioprotective materials for shielding organisms from radiations.

The polyamino acid for use in the invention may be prepared by any process presently known or developed in the future without limitation. Useful processes include, for example: (1) a process comprising preparing a polymer solution by dissolving a solid polyamino acid in an organic solvent or by carrying out homogeneous polymerization of N-carboxyamino acid anhydride(s) (amino acid-N-carboxylic acid anhydride(s): amino acid-NCA(s)) in an organic solvent, adding water and an emulsifier to emulsify the polymer solution, and then removing the organic solvent ("re-emulsification process" disclosed in Japanese Examined Patent Publication No. 1993-13168); (2) a process in which amino acid-NCA(s) is polymerized using an organic solvent capable of dissolving amino acid-NCAs but incapable of dissolving polyamino acids, to thereby form polyamino acid particles ("precipitation polymerization process" disclosed in Japanese Unexamined Patent Publication No. 1976-87597); (3) a process in which amino acid-NCA(s) as solid phase is polymerized without any organic solvent, to obtain a polyamino acid powder ("solid phase polymerization process" disclosed in Japanese Unexamined Patent Publication No. 1991-95223); (4) a process comprising dissolving amino acid-NCA(s) in an organic solvent capable of dissolving amino acid-NCAs but incapable of dissolving polyamino acids, dispersing the solution in another organic solvent incompatible with the solution, and carrying out polymerization in that state to obtain polyamino acid particles ("heterogeneous polymerization process" disclosed in Japanese Unexamined Patent Publication No. 1992-41526); (5) a process comprising dissolving amino acid-NCA(s) in an anhydrous halogenated hydrocarbon solvent or like organic solvent, and performing polymerization in a homogeneous solution using a polymerization initiator, typically an amine compound ("homogeneous solution polymerization process"); and (6) a process in which a hydrophobic organic solvent phase containing amino acid-NCA(s) dissolved therein is contacted with an aqueous phase containing a polymerization initiator dissolved therein, to polymerize the amino acid-NCA(s) at the interface between the two phases (Japanese Unexamined Patent Publication No. 1974-57096). Further, processes for preparing polyamino acids as emulsions have recently become known, which include, for example: polymerization of α-amino acid-NCA(s) in water containing a polymerization initiator and an emulsifier (Japanese Unexamined Patent Publication No. 1997-183842); and a process comprising emulsifying at least water and an organic solvent having a water solubility not greater than 10 g/100 mL to prepare an oil-in-water type base emulsion which provides a place for polymerization, adding α-amino acid-NCA(s) to the base emulsion to carry out polymerization, and removing the organic solvent (Japanese Unexamined Patent Publication No. 1996-127652). Polymer particles in the emulsion thus obtained can be separated from the water to obtain polyamino particles.

Amino acid NCAs useful as monomers in the above processes include all amino acid-NCAs derived from α-amino acids. When an amino acid-NCA is prepared using an α-amino acid having, in its side chain, a functional group such as carboxyl, hydroxyl, thiol, amino, guanidinyl or the like, the functional group needs to be protected with a suitable protective group before converting the α-amino acid into an amino acid-NCA.

Specific examples of α-amino acids include (a) neutral amino acids such as glycine, alanine, valine, norvaline, leucine, isoleucine, norleucine, phenylalanine, methionine, proline, asparagine, glutamine, tryptophan and the like, (b) acidic amino acids such as glutamic acid, aspartic acid and the like, and their esters ("esters" means methyl ester, ethyl ester, propyl ester, butyl ester, octyl ester, 2-ethylhexyl ester, cyclohexyl ester, phenyl ester, benzyl ester and the like), (c) basic amino acids such as lysine, arginine, histidine and the like, and N-acyl basic amino acids such as N-carbobenzoxylysine, N-carbobenzoxyornithine, N-acetyllysine and the like, and (d) hydroxyl-containing α-amino acids such as serine, threonine, cysteine, tyrosine and the like and their esters ("esters" means methyl ester, ethyl ester, propyl ester, butyl ester, octyl ester, 2-ethylhexyl ester, cyclohexyl ester, phenyl ester, benzyl ester and the like). Among them, water-soluble α-amino acids are preferred.

Amino acid-NCAs obtained from these α-amino acids may be optically active substances, racemic modifications or mixtures thereof. These amino acid-NCAs can be used in combination, as required.

The constituent amino acid(s) of the polyamino acid(s) for use in the invention are not limited, but it is preferable that the polyamino acid(s) comprises at least one amino acid selected from the group consisting of glutamic acid, phenylalanine, alanine and leucine. The polyamino acid(s) comprising at least one of these amino acids may be homopolymer(s) of one of these amino acids or copolymer(s) of any of these amino acids and other amino acid(s) such as aspartic acid or the like.

Preferably, these polymers have a weight average molecular weight of 1,000 to 1000,000 from the viewpoint of formability. A more preferable weight average molecular weight is 20,000 to 500,000, in particular 50,000 to 300,000.

In the present invention, derivative(s) of polyamino acid(s) can be used in place of or in combination with the polyamino acid(s). Examples of polyamino acid derivatives include, but are not limited to, polyamino acid esters, and copolymers comprising polyamino acids and other polymers.

A polyamino acid ester can be obtained by homogeneous solution polymerization of amino acid ester-N-carboxylic acid anhydride(s) (amino acid-NCA(s)) having 2 or more, preferably 2 to 20, aliphatic ester groups, in a mixed solvent of an acetic acid ester and an aromatic hydrocarbon, using a polymerization initiator. Examples of amino acid-NCAs having aliphatic ester groups (—COOR groups) include glutamic acid-γ-ester-NCA and aspartic acid-β-ester-NCA ("ester groups" means $C_2$ to $C_{20}$, preferably $C_2$ to $C_{16}$, aliphatic hydrocarbon groups represented by —COOR wherein R is ethyl, butyl, cyclohexyl, octyl, stearyl or the like). These amino acid-NCAs may be optically active substances, racemic modifications or a mixture thereof. If necessary, two or more of these amino acid-NCAs may be mixed to form a copolymer. Examples of aromatic hydrocarbons include benzene, toluene, xylene, mesitylene and like $C_6$ to $C_{16}$, preferably $C_6$ to $C_{12}$, benzene or lower alkyl-substituted benzene. Examples of acetic acid esters include those of methyl, ethyl, propyl, butyl, hexyl, octyl or like $C_1$ to $C_{20}$ hydrocarbon. As the polymerization initiator, any known compound usable for polymerization of N-carboxyamino acid anhydrides can be used without limitation. It is preferable to use an amine compound or metal alcoholate.

The polyamino acid(s) or derivative(s) thereof obtained in the above manner can be made into a powder by a known re-emulsification process or like process.

Commercially available polyamino acids or derivatives thereof can be used for convenience. The following are examples of commercially available polyamino acids and derivatives thereof; poly-DL-alanine, poly-β-alanine, poly-L-arginine and its salts (e.g., hydrochloride and sulfate), poly-L-asparagine, poly(α,β)-DL-aspartic acid and its salts (e.g., Na), poly-L-aspartic acid and its salts (e.g., Na), poly-β-benzyl-L-aspartate, poly-S-benzyl-L-cystein, poly-γ-benzyl-L-glutamate, poly-im-benzyl-L-histidine, poly-S-CBZ-L-cystein, poly-ε-CBZ-D-lysine, poly-ε-CBZ-DL-lysine, poly-ε-CBZ-L-lysine, poly-δ -CBZ-DL-ornithine, poly-O-CBZ-L-serine, poly-O-CBZ-D-thyrosin, poly-γ-ethyl-L-glutamate, poly-D-glutamic acid and its salts (e.g., Na), poly-L-glutamic acid and its salts (e.g., Na), poly-γ-n-hexyl-L-glutamate, poly-L-histidine and its salts (e.g., hydrochloride), poly{α,β[N-(2-hydroxyethyl)-DL-aspartic amide]}, poly-L-hydroxyproline, poly-{α,β[N-(3-hydroxypropyl)-DL-aspartic amide]}, poly-$N^5$-(3-hydroxypropyl)-L-glutamine, poly-L-isoleucine, poly-L-leucine, poly-D-lysine and its salts (e.g., hydrochloride), poly-DL-lysine and its salts (e.g., hydrobromide), poly-L-lysine and its salts (e.g., hydrobromide), poly-L-lysine agarose, succinoylated poly-L-lysine, poly-γ-methyl-L-glutamate, poly-DL-ornithine and its salts (e.g., hydrobromide), poly-L-ornithine and its salts (e.g., hydrobromide), poly-L-phenylalanine, poly-L-proline, poly-DL-serine, poly-L-serine, poly-L-threonine, poly-DL-tryptophan, poly-L-tryptophan, poly-D-tyrosine, poly-L-tyrosine, random copolymers of L-arginine (poly [Arg,Ser]3:1, poly[Arg,Trp]4:1, poly[Arg,Pro,Thr]1:1:1, poly[Arg,Pro, Thr]6:3:1), random copolymers of D-glutamic acid (poly[D-Glu,D-Lys]6:4), random copolymers of L-glutamic acid (poly[Ala,Glu,Lys,Tyr]6:2:5:1, poly[Glu,Glt-OEt]1:1, poly[Glu,Glu-OMe]4:1, poly[Glu,Ala]6:4, poly[Glu,Ala,Tyr]1:1:1, poly[Glu,Ala,Tyr]6:3:1, poly[Glu,Leu]4:1, poly[Glu,Lys,Tyr]6:3:1, poly[Glu,Lys]1:4, poly[Glu,Phe]4:1, poly[Glu,Tyr]1:1, poly[Glu,Tyr]4:1), random copolymers of L-lysine (poly[Lys,Ala,Glu, Tyr]5:6:2:1, poly[Lys,Phe]1:1, poly[Lys,Ser]3:1, poly[Lys,Trp]4:1, poly[Lys,Tyr]4:1, poly[Lys,Tyr]1:1, poly[Lys,Tyr]1:9), random copolymers of L-ornithine (poly[Orn,Leu]1:1, poly [Orn,Ser]1:1, poly[Orn,Trp]4:1, poly[Orn,Tyr]4:1), and poly(Pro-Gly-Pro). These polyamino acids are commercially available from Sigma.

The polyamino acid(s) or derivative(s) thereof for use in the invention may be further modified with a sugar component or a polyhydric alcohol to improve the radioprotective activity, so that the material of the invention is likely to be used as a more effective radioprotective agent.

Polyhydric alcohols useful for the modification include, for example, glycerin, sorbitol, sorbitan and pentaerythritol.

Sugar components useful for the modification include, for example, arabinose, xylose, ribose, glucose, galactose, mannose, fructose, sucrose, trehalose and like monosaccharides, and oligosaccharides containing these monosaccharides. Preferred oligosaccharides include, but are not limited to, degraded mannans.

Degraded mannans usable in the invention can be obtained by degrading any of various mannans by a desired process. Mannans are polysaccharides mainly consisting of mannose. Examples of mannans include the following:
1. Plant-derived mannans: Including copra meal and flakes obtained from coconuts, Huacra Palm (a plant of the palm family grown in South Africa), tsukuneimo (a type of yam) mannan, yamaimo (Japanese yam) mannan, etc.
2. Glucomannans: Polysaccharides comprising glucose and mannose, including mannans obtained from konjak, lilies, daffodils and subterranean stems of *Lycoris radiata*.
3. Galactomannans: Polysaccharides comprising galactose and mannose, including mannans obtained from locust bean gum, soybean hulls derived from soybean seed coat, tamson gum, tara gum, guar gum or the like.
4. Mannans comprising at least two types of sugars other than mannose, including D-galacto-D-gluco-D-mannan contained in xylems of conifers, and mannans obtained from xanthan gum or the like.

Known processes for degrading mannans include, for example, a biochemical degradation process directly using polysaccharide degrading enzymes (such as mannase, galactomannase, glucomannase or the like) or microbes producing any of these enzymes; a chemical degradation process using an acid, alkali or the like; and a physical decomposition process using high-speed stirring, a shearing machine or the like. A wide variety of mannans degraded by these processes are usable in the invention. The degraded mannan for use in the invention may be a product obtainable by any of the above degradation processes, and need not be a product actually produced by these processes.

Specific examples of degraded mannans include β-1,4-mannobiose, β-1,4-mannotriose, β-1,4-mannotetraose, methyl β-mannoside and like β-1,4-mannooligosaccharides; β-1,6-galactomannooligosaccharide, β-1,4-galactomannnooligosaccharide, α-1,6-galactomannooligosaccharide, α-1,3-galactomannooligosaccharide and like mannooligosaccharides in which one or two galactose molecules are bonded to β-1,4-mannobiose, β-1,4-mannotriose or β-1,4-mannotetraose to form branched structure; degraded galactomannans such as oligosaccharides obtained by decomposing copra residues, coffee residues, guar gum or locust bean gum with mannase; oligosaccharides in which glucose or maltose is bonded to mannotriose, mannotetraose or the like via β-1,4 linkage; and degraded products of glucomannans contained in konjak.

Commercially available degraded mannans can be used in the invention for convenience. Further, a degraded galactomannan can be obtained, for example, by: extracting a galactomannan from seeds of locust, tara or guar plants by water extraction, alcohol precipitation or like method, degrading the extract with acid(s) or enzyme(s) such as galactomannase, and separating a fraction having a molecular weight of 5,000 to 50,000, preferably 10,000 to 20,000. A degraded glucomannan can also be obtained by swelling a konjak powder with water to form a konjak paste, and degrading the paste with glucomannase. These degraded mannans may be purified products or crudely purified products, and may be in the form of aqueous solutions or like liquids, powders, granules or like solids, or dry products.

In the present invention, derivatives of the degraded mannans may be used as oligosaccharides. These derivatives include a wide variety of substances produced by bonding hemiacetalic hydroxyl group(s) of a degraded mannan with a substance other than saccharides by dehydration condensation reaction. Examples the derivatives include isopropylidene derivatives, benzylidene derivatives, butylene glycol derivatives, polyhydric alcohol derivatives, and pyrrolidone derivatives.

The method for modifying the polyamino acid or derivative thereof with a sugar component is not limited and may be any method conventionally used for sugar modification.

The radioprotective material of the invention prepared using the above components may be used as it is. Alternatively, the material, as it is or after being polymerized or mixed with a biodegradable plastic or like biodegradable polymer, may be molded into various shapes by hot extrusion molding, casting or like process. As the biodegradable polymer, any biodegradable polymer presently known or developed in the future can be used. Examples of biodegradable polymers presently marketed or experimentally produced include microbial biodegradable plastics available under the tradenames "Biopol" (polyhydroxybutylate/hydroxyvalerate copolymer, Japan Monsanto Co., Ltd.) and "Biogeen" (polyhydroxybutylate, Mitsubishi Gas Chemical Co., Inc.) and the like; natural biodegradable plastics available under the tradenames "Mata-bi" (starch/polylactic acid, The Nippon Synthetic Chemical Industry Co., Ltd.), "Cornpol" (modified starch, Nippon Cornstarch), "Celgreen PCA" (cellulose acetate, Daicel Chemical Industries, Ltd.), "Dolon CC" (chitosan/cellulose/starch, Aicello Chemical Co., Ltd.) and the like; synthetic biodegradable plastics available under the tradenames "Lactee" (polylactic acid, Shimadzu Corp.), "Lacea" (polylactic acid, Mitsui Chemicals, Inc.), "Eco-PLA" (polylactic acid, Cargil-Dow), "Celgreen" (cellulose acetate plastic, Daicel Chemical Industries, Ltd.), "Celgreen P-H, P-HB" (polycaprolactone, Daicel Chemical Industries, Ltd.), "Bionolle" (polybutylene succinate, polybutylene succinate/adipate copolymer, Showa Highpolymer Co., Ltd.), "Yupec" (polybutylene succinate carbonate, Mitsubishi Gas Chemical Co., Inc.), "Lunare SE" (polyethylene succinate, Nippon Shokubai Co., Ltd.), "Poval" (polyvinyl alcohol, Kuraray Co., Ltd.) and the like.

The radioprotective material of the invention may be dissolved in a solvent and formed into a membrane, sheet, film or the like. The radioprotective material of the invention, as it is or after being dissolved in a solvent, can be made into a coating agent, which can be applied to a film, sheet or like product. The resulting film, sheet or the like can be used for packaging, coating, or radioprotection (radiation shielding) of items that are prone to be damaged by radiation, such as agricultural and marine products, foods, domestic animals, human bodies, electrical precision equipment and the like.

The radioprotective material of the invention, as it is or after being bonded to or immobilized on particles (beads), can be added to a cosmetic preparation and mixed with cosmetic components, to provide a radiation (ultraviolet) blocking cosmetic product which protects the exposed skin of the face, hand, etc., from radiations (Ultraviolet-A, Ultraviolet-C, alpha rays or beta rays) emitted from the atmosphere, electric or electronic equipment or the like. Further, the material of the invention may be kneaded directly into fibers (spinning components), or applied, adhered or bonded onto fiber surfaces, to provide fibers or a fiber product such as clothes (radioprotective fiber product) that can block or reduce effects of radiations emitted from the atmosphere, the earth's surface, electric or electronic equipment or the like.

The radioprotective material of the invention can be used in radiation therapy or radiographic inspection, in order to reduce adverse effects of radiations on non-affected part and to thereby protect the body. For this purpose, the material of the invention may be used as it is or as a radioprotective preparation (e.g., an external preparation (a coating preparation such as a cream, gel or the like, or a patch), a non-oral preparation (an injection, suppository or enteric preparation)) formulated in a routine manner. The material of the invention, as it is or after being suitably processed, can be used as a medical or experimental radiation-resistant material which prevents medical or experimental substances including enzymes, cells, living tissues and like biomaterials, from being functionally deteriorated by radiation sterilization. For use as a radiation-resistant material, the material of the invention is mixed with or immobilized on any of the above biomaterials, or processed into a form (such as a coating agent, sheet, film or the like) capable of covering the biomaterials.

Thus, the present invention also provides a method for blocking or reducing adverse effects of radiations on an object, in which the radioprotective material is added to, mixed with, placed over or immobilized on the object. Further, the radioprotective products, for example those mentioned above, which are obtained by adding, mixing, placing or immobilizing the radioprotective material, can be placed (covered, coated or immobilized) over an object to be protected from adverse effects of radiations, or administered (externally administered, orally administered, inoculated or ingested) to the object, in order to prevent the object from being functionally deteriorated or damaged by radiations.

Generally, materials used to block effects of radiations and thereby protect an object from radiations are required to have a high density, no crystallinity, a high molecular weight, and heat resistance. This is because radiations such as beta rays or gamma rays, which are transmitted through the particles of the materials, are difficult to be transmitted through materials with amorphous matrix structure. Also, since Ultraviolet-B, Ultraviolet-C and alpha rays generate heat when they hit a material, materials to be used for blocking these radiations need to be heat resistant. Since the radioprotective material of the invention mainly comprises polyamino acid(s), the material has a high molecular weight and is heat resistant, and thus is suitable for the above purposes. Further, the material is preferable for blocking radiations, in particular for protecting organisms from radiations, owing to its excellent biocompatibility and non-antigenicity.

EXAMPLES

The following Examples and Experiments are provided to illustrate the invention in detail and are not to limit the scope of the claims of the invention.

Example 1

Production of α-polyglutamic Acid

γ-Benzyl-L-polyglutamate (γ-BLG, Ajinomoto Co., Inc.) was phosgenated in tetrahydrofuran to synthesize an N-carboxyamino acid anhydride of γ-BLG, which was then recrystallized several times for purification. The purified product was dissolved in a mixed solvent of dioxane/methylene chloride, and polymerized in the presence of triethylamine as an initiator, giving poly-γ-benzyl-L-glutamate (PBLG) The PBLG was then treated with anhydrous HBr to give α-polyglutamic acid.

Example 2

A *Bacillus natto* strain isolated from commercially available natto (fermented soybeans) was inoculated into a culture medium containing 10 g/L of peptone (Daigo Eiyou), 10 g/L of meat extract (Daigo Eiyou) and 10 g/L of dextrin (Daigo Eiyou), and incubated for 48 hours at 30° C. under aerated conditions. The resulting culture solution was separated into a solid and liquid with a centrifuge. A 90% ethanol solution was added to the separated liquid. The resulting precipitates were washed with water, and then repeatedly washed with an ethanol solution, giving γ-polyglutamic acid (γ-PGA).

Experiment 1

Ten mg of papain (Merck) was dissolved per 1 ml of distilled water to obtain 4 ml of a papain solution. The papain solution was dispensed in 0.2 ml aliquots into four 10 ml glass test tubes. Into each of these test tubes were placed, as a radioprotective material, α-polyglutamic acid (α-PGA) synthesized by the NCA method in Example 1, polyglucosylacryl ethyl methacrylate (GEMA)(Nippon Fine Chemical Co., Ltd.) and glucose, each to a final concentration of 1.25 wt. % (total concentration: 3.75 wt. %). The test tubes were irradiated with different doses of gamma rays (0, 5, 10 and 15 kGy), and then the residual papain activity of the irradiated solution was measured. As a control test, a papain solution which did not contain the radioprotective material was irradiated with gamma rays in the same manner as above, and the residual papain activity of the irradiated solution was measured.

The papain activity was measured in the following manner. The gamma ray-irradiated enzyme solution was suitably diluted, and 1 ml of the diluted solution was added to 1 ml of 2.5% casein (PBS buffer solution (pH 7.4)). Further, 1 ml of a 15 mM cysteine solution (PBS buffer solution (pH 7.4)) was added, followed by reaction at 37° C. for 30 minutes. Then, a 16% trichloroacetic acid solution was added to stop the reaction. The reaction mixture was centrifuged (at 20,000 rpm for 15 minutes) to remove precipitates. The absorbance (280 nm) of the obtained supernatant was measured to determine the enzyme activity. Then, from the change in enzyme activity by gamma ray irradiation, the radiation (gamma ray) protective effect of the mixture of α-PGA, GEMA and glucose was evaluated.

Figure 1:
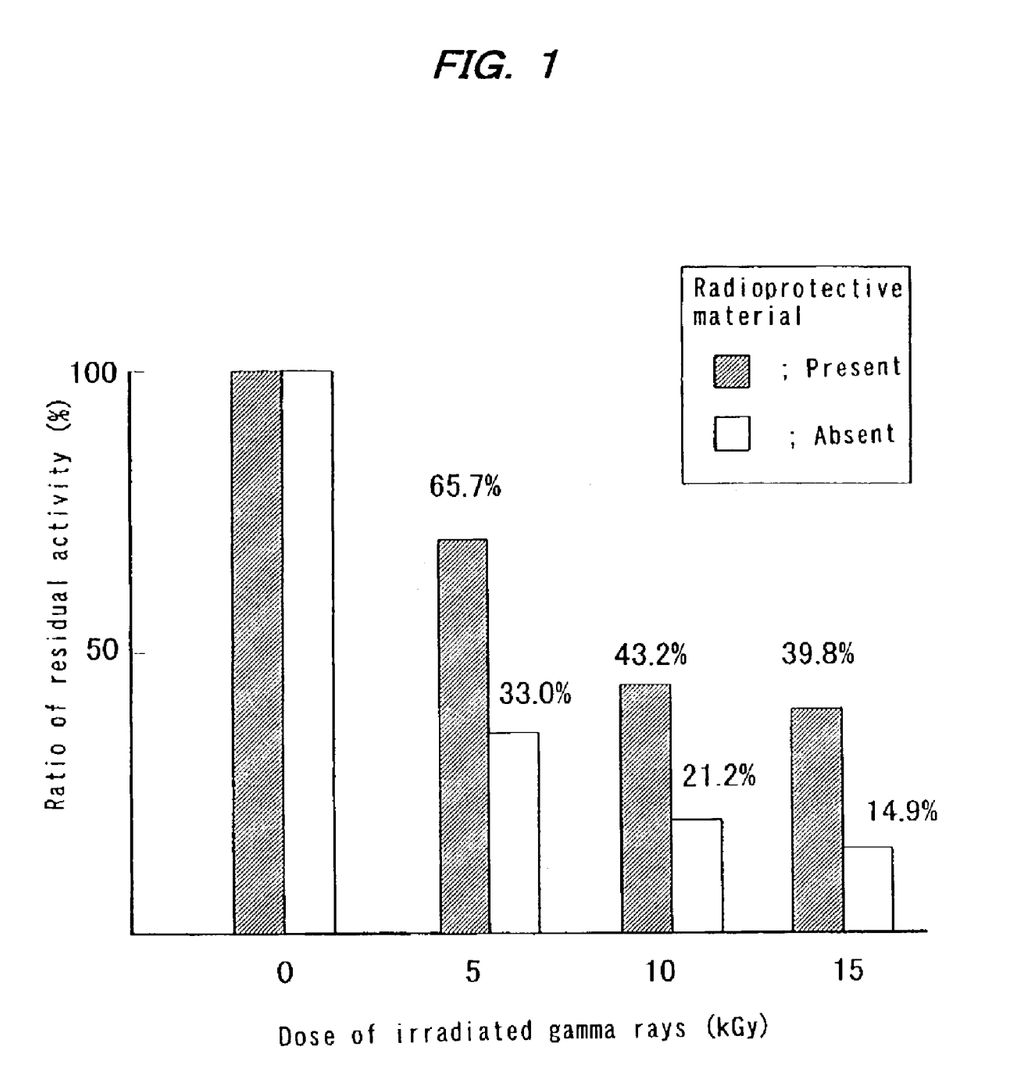
FIG. 1 shows the results of Experiment 1 in which the residual papain activity was measured after irradiation with gamma rays (at doses of 0, 5, 10 and 15 kGy) using a mixture of α-polyglutamic acid (α-PGA), polyglucosyl acryl ethyl methacrylate (GEMA) and glucose as a radioprotective material for papain.

FIG. 1 shows the results. The results reveal that the mixture of α-PGA, GEMA and glucose has a radiation (gamma ray) protective effect. In particular, even after irradiation with 15 kGy of gamma rays, as much as about 40% of the papain activity remained.

Experiment 2

Figure 2:
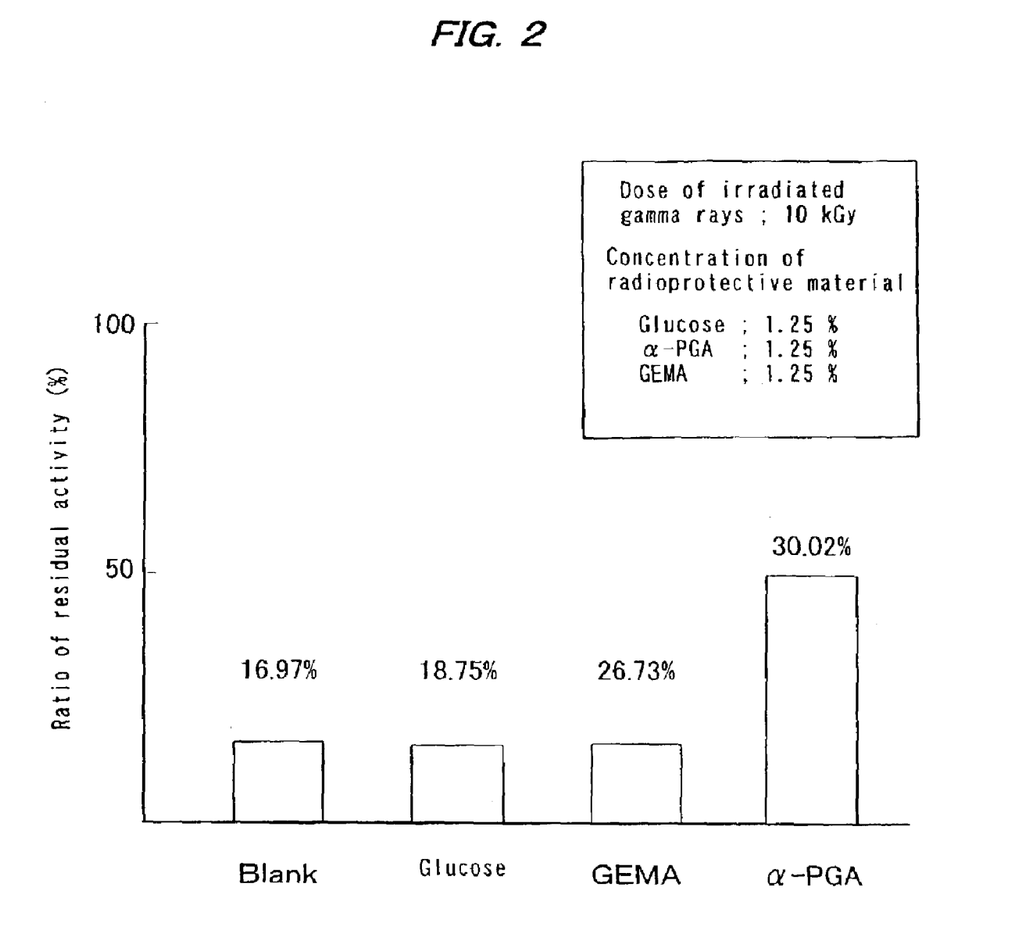
FIG. 2 shows the results of Experiment 2 in which the residual papain activity was measured after irradiation with gamma rays (at a dose of 10 kGy) using each of α-PGA, GEMA and glucose singly as a radioprotective material for papain.

Four glass test tubes each containing 0.2 ml of a papain solution were prepared in the same manner as in Experiment 1. As a radioprotective material, each of α-PGA, GEMA and glucose was placed into one of three of the above test tubes, achieving a final concentration of 1.25 wt. %. The other test tube containing no radioprotective material was used for a control test. Each tube was irradiated with 10 kGy of gamma rays in a manner similar to that in Experiment 1. Then, the enzyme activity after irradiation was measured to determine the radiation (gamma ray) protective effects of α-PGA, GEMA and glucose. FIG. 2 shows the results. The results reveal that α-PGA has an excellent radiation (gamma rays) protective effect.

Experiment 3

Figure 3:
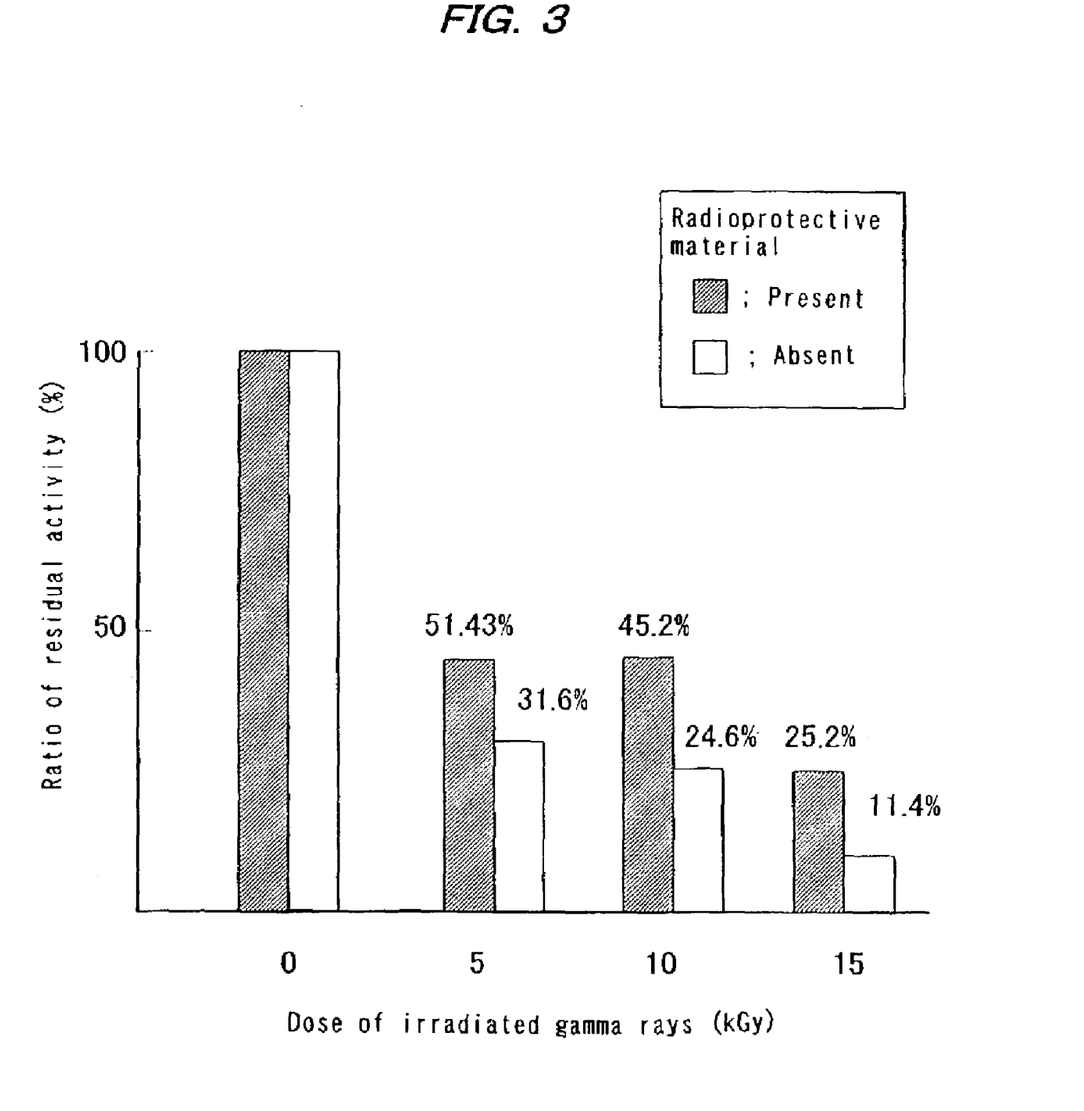
FIG. 3 shows the results of Experiment 3 in which the residual papain activity was measured after irradiation with gamma rays (at doses of 0, 5, 10 and 15 kGy) using α-PGA as a radioprotective material for papain.

In view of the results of Experiment 2, a papain solution containing α-PGA (at a final concentration of 1.25 wt. %) was prepared, and irradiated with different doses of gamma rays (0, 5, 10 and 15 kGy) to evaluate the radiation (gamma rays) protective effect of α-PGA. FIG. 3 shows the results.

Experiment 4

Figure 4:
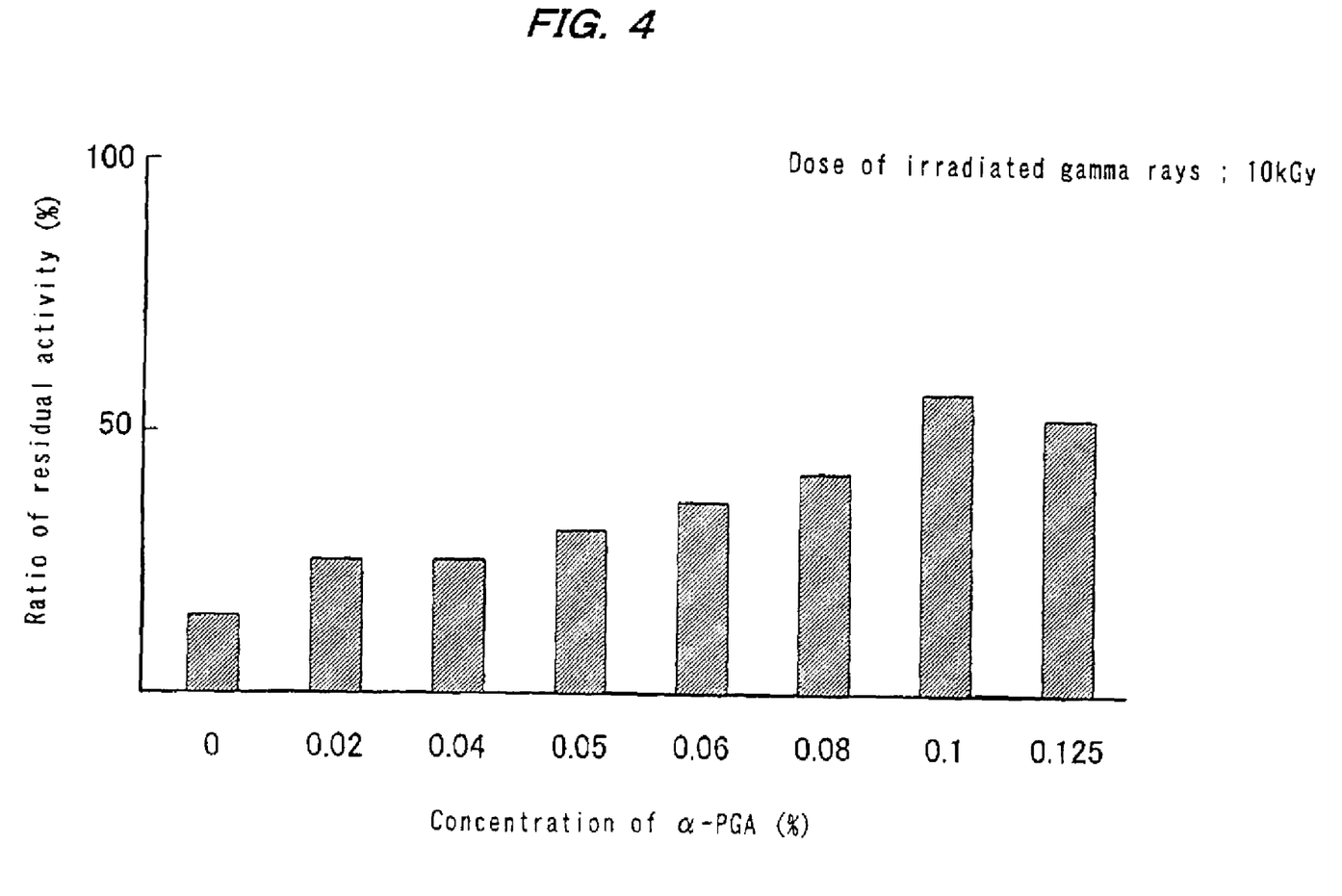
FIG. 4 shows the results of Experiment 4 in which the residual papain activity was measured after irradiation with gamma rays (10 kGy) using α-PGA at various concentrations as a radioprotective material for papain.

In order to measure the α-PGA concentration dependence of the radiation (gamma rays) protective effect of α-PGA, papain solutions containing α-PGA at final concentrations ranging from 0 to 0.125 wt. % were prepared in the same manner as in Experiment 1 and irradiated with gamma rays (10 kGy), to evaluate the radiation (gamma ray) protective effect of α-PGA. FIG. 4 shows the results.

Experiment 5

Each of three radioprotective material liquids (α-PGA, GEMA and glucose) was added singly to 1 ml portions of α-amylase (C.P.R Co. Ltd., enzyme activity: 8,000 U/ml) to final concentrations of 0 wt. %, 0.5 wt. %, 1.25 wt. % and 2.5 wt. %. The resulting solutions were irradiated with gamma rays (10 kGy), and the residual α-amylase activity of the irradiated solutions was measured.

The measurement of the α-amylase activity was carried out in the following manner: The gamma ray-irradiated enzyme solutions were suitably diluted, and each diluted solution (1 ml) was added to 20 ml of a 1 wt. % potato starch solution, followed by reaction at 40° C. The end of the reaction was detected by reaction with an iodine solution, taking the time at which iodine-starch reaction was negative as the end of the reaction. From the time required until the end of the reaction, the enzyme activity was calculated according to the following equation:

$$\text{Activity} = 200 \times \frac{\text{Dilution ratio of gamma ray-irradiated enzyme solution}}{\text{Time required until the end of reaction}}$$

Figure 5:
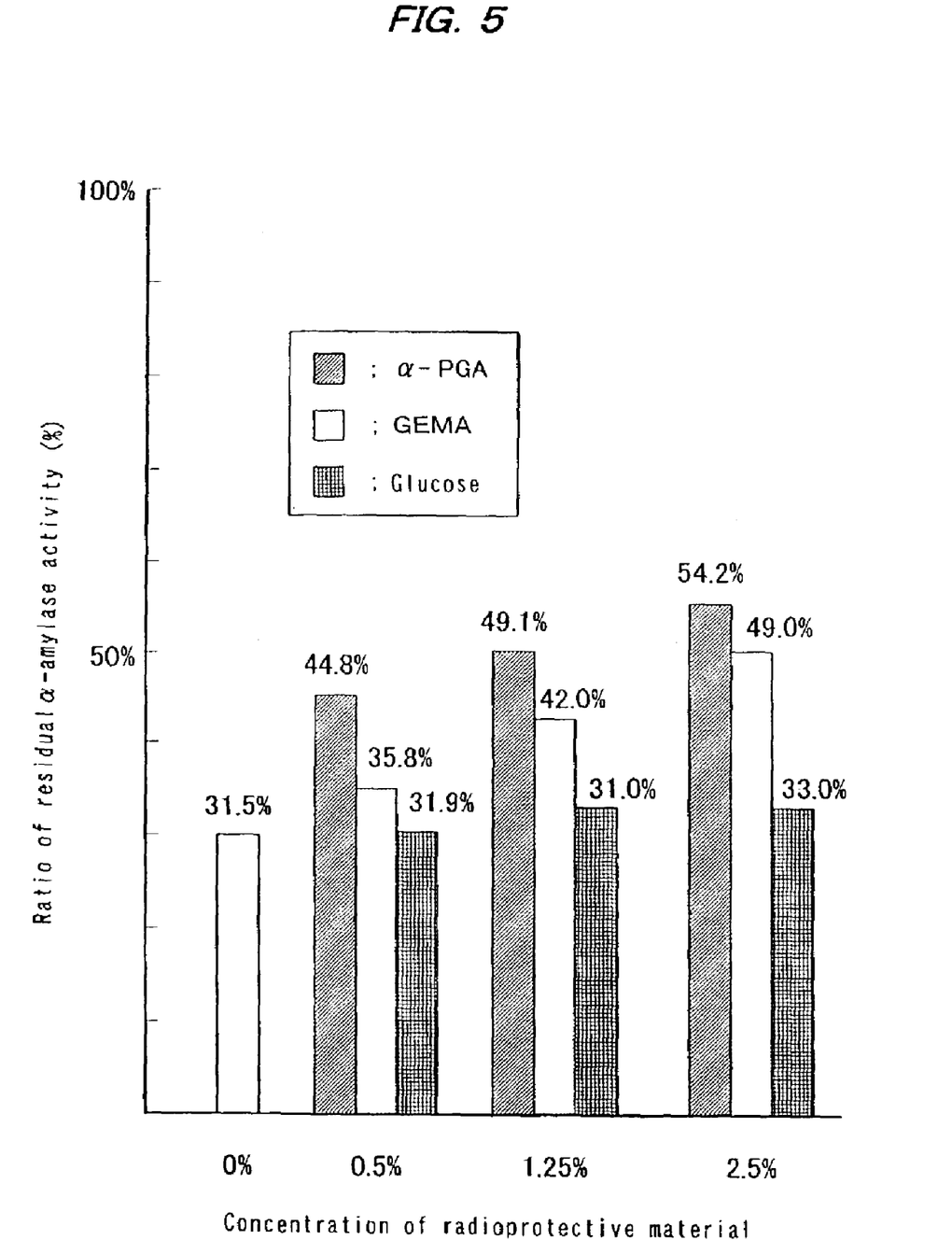
FIG. 5 shows the results of Experiment 5 in which the residual α-amylase activity was measured after irradiation with gamma rays (10 kGy) using each of α-PGA, GEMA and glucose singly (at concentrations of 0%, 0.5%, 1.25% and 2.5%) as a radioprotective material for α-amylase.

FIG. 5 shows the results.

The results reveal that α-PGA significantly inhibits the α-amylase activity reduction caused by gamma ray radiation, demonstrating that α-polyglutamic acid has a high protective effect against gamma rays.

Experiment 6

Each of three radioprotective material liquids (α-PGA, GEMA and glucose) was added singly to 1 ml portions of α-amylase (C.P.R Co. Ltd., enzyme activity: 8,000 U/ml) to final concentrations of 0 wt. %, 0.5 wt. %, 1.25 wt. % and 2.5 wt. %. The resulting solutions were irradiated with UV for time periods ranging from 0 to 5 hours. Then, the residual α-amylase activity of the irradiated solutions was measured. As a control test, an aqueous α-amylase solution containing no radioprotective material was irradiated with UV in the same manner as above to measure the residual α-amylase activity.

Figure 6:
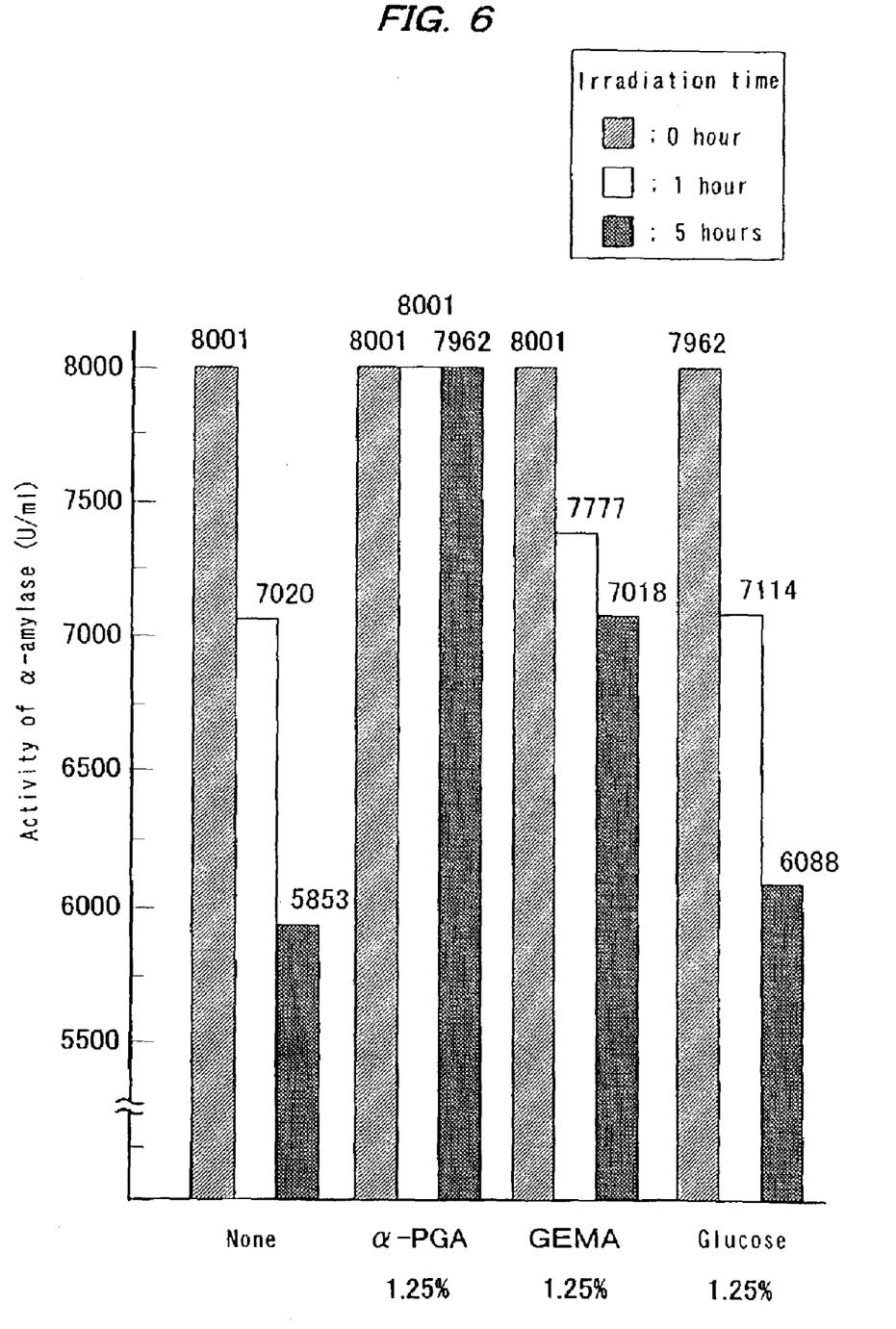
FIG. 6 shows the results of Experiment 6 in which the residual α-amylase activity was measured after irradiation with ultraviolet rays (15 W) for 0, 1 and 5 hours using each of α-PGA, GEMA and glucose singly (at a concentration of 1.25%) as a radioprotective material for α-amylase.

The measurement was carried out in the following manner: First, 0.2 ml of a test solution was applied to the surface of a slide glass; dried at room temperature, and irradiated with an ultraviolet lamp (15 W) from 15 cm above the surface of the slide glass. After irradiation, the dried enzyme solution on the slide glass was dissolved in 0.2 ml of distilled water, and the α-amylase activity of the resulting solution was measured in the same manner as in Experiment 5. FIG. 6 shows the results. The results reveal that when α-polyglutamic acid is used as a radioprotective material, the α-amylase activity was scarcely reduced by UV radiation, demonstrating that α-polyglutamic acid has a remarkably high protective effect against UV radiation.

Experiment 7

Figure 7:
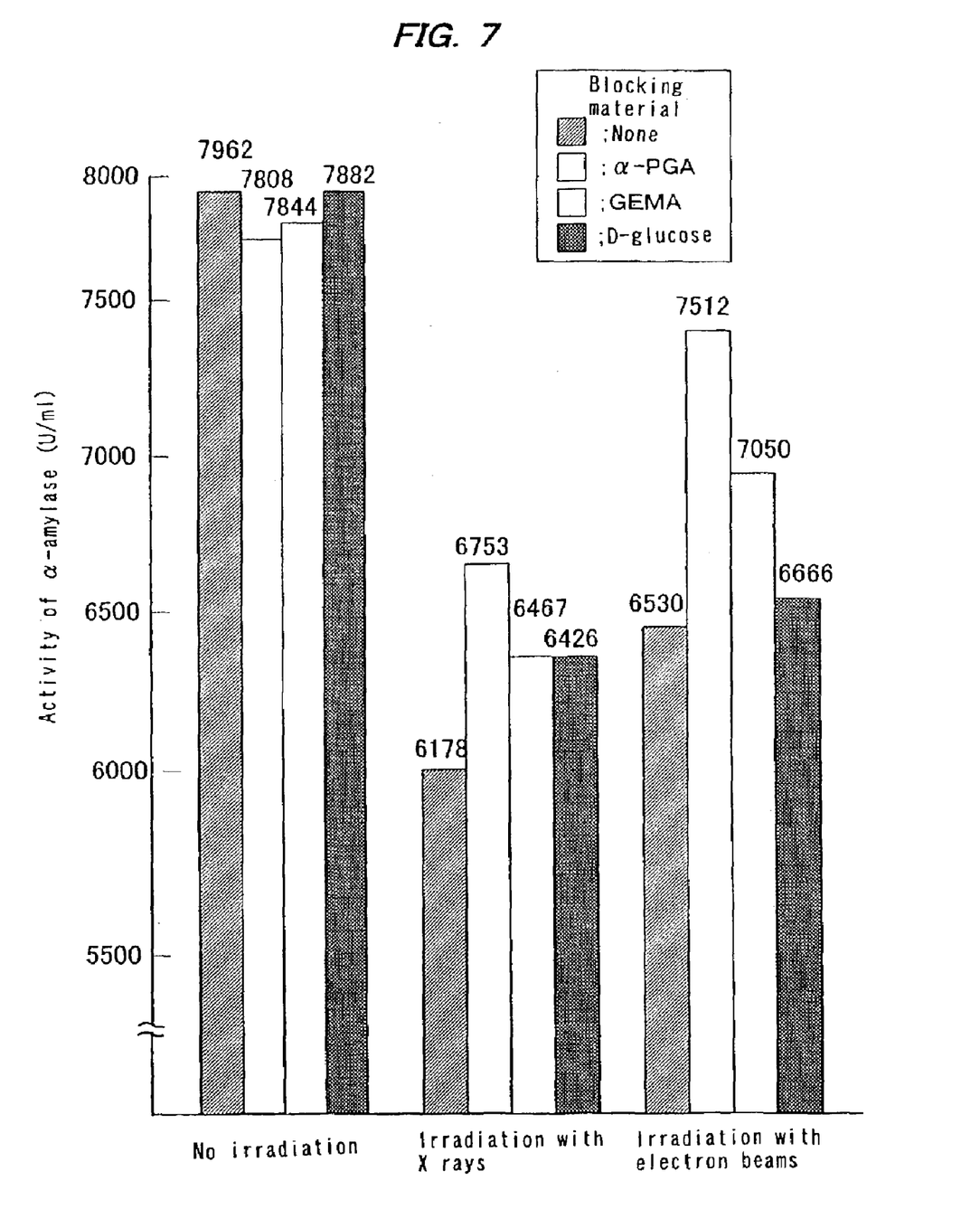
FIG. 7 shows the results of Experiment 7 in which the residual α-amylase activity was measured after irradiation with X rays (10 kGy) or electron beams (10 kGy) using each of α-PGA, GEMA and glucose singly (at a concentration of 1.25%) as a radioprotective material for α-amylase.

Each of three radioprotective materials (α-PGA, GEMA and glucose) was added singly to 1 ml of α-amylase (C.P.R Co. Ltd., enzyme activity: 8,000 U/ml) to a final concentration of 1.25 wt. %. Using the resulting solutions, slide glass samples were prepared in the same manner as in Experiment 6, and each irradiated with X rays (10 kGy) or electron beams (10 kGy). Then, the residual α-amylase activity was measured in the same manner as in Experiment 6. As a control test, α-amylase without radioprotective materials was irradiated in the same manner as above to measure the residual α-amylase activity. FIG. 7 shows the results. The results reveal that α-polyglutamic acid remarkably diminishes the α-amylase activity reduction caused by irradiation with X rays or electron beams, demonstrating that α-polyglutamic acid has an extremely high protective effect against these radiations.

Experiment 8

Figure 8:
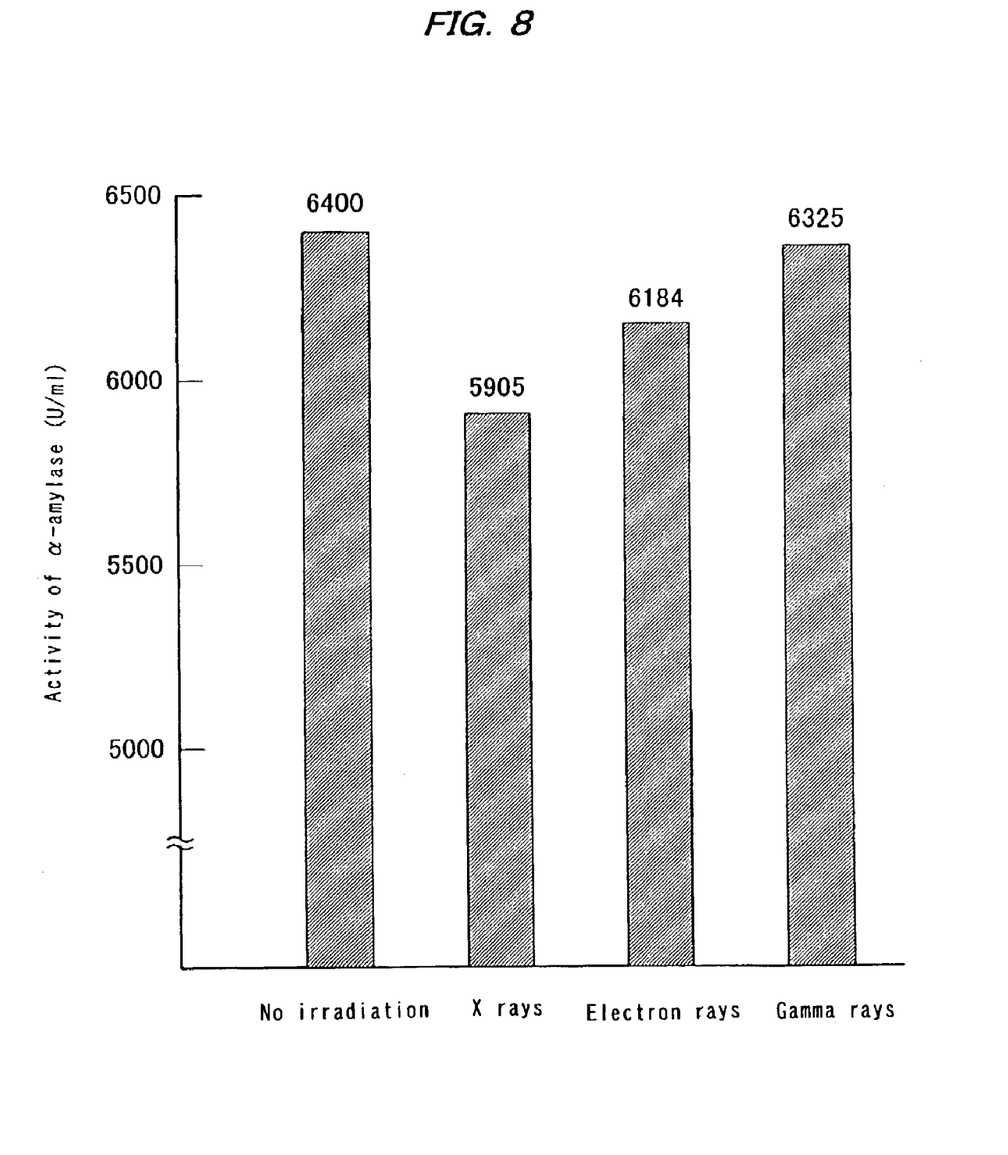
FIG. 8 shows the results of Experiment 8 in which the residual α-amylase activity was measured after irradiation with X rays (10 kGy), electron beams (10 kGy) or gamma rays (10 kGy) using γ-PGA (at a concentration of 1.25%) as a radioprotective material for α-amylase.

Slide glass samples were prepared in the same manner as in Experiment 6, using a solution consisting of α-amylase and a radioprotective material (γ-PGA of Example 2 at a final concentration of 1.25 wt. %). Each slide glass sample was irradiated with X rays (10 kGy), electron beams (10 kGy) or gamma rays (10 kGy). Then, the residual α-amylase activity was measured in the same manner as in Experiment 6. FIG. 8 shows the results. The results reveal that, like α-polyglutamic acid, γ-polyglutamic acid has an extremely high protective effect against X rays, electron beams and gamma rays.

INDUSTRIAL APPLICABILITY

The radioprotective material of the invention blocks effects of various radiations, and therefore is capable of significantly preventing possible radiation exposure that may occur in nuclear power facilities, medical facilities, aircrafts in flight or uranium ore refineries, or may be caused by radiography at construction sites. Moreover, the material of the invention is capable of protecting organisms or articles such as precision equipment, photographic dry plates or the like from damages caused by radiations emitted from experimental equipment, color televisions or like electric appliances containing radiation tubes, or by radiations from outer space or the earth's crust. Further, the radioprotective material of the invention, which is biodegradable into nontoxic substances, is valuable from the viewpoint of environmental conservation.

The invention claimed is:

1. A radioprotective product comprising a radioprotective material comprising a polyamino acid or polyamino acids or at least one derivative selected from the group consisting of polyamino acid esters, and copolymers comprising polyamino acids and other polymers (except for polyamino acid compounds in which a residue of aminobenzaldehyde semicarbazone or aminobenzaldehyde thiosemicarbazone is bonded to carboxylic acid at the ω-position of polyglutamic acid or polyaspartic acid).

2. A radioprotective product according to claim 1, which is at least one member selected from the group consisting of radioprotective films, radioprotective sheets, radioprotective coating agents, radioprotective cosmetic products, radioprotective fiber products, radioprotective preparations and radiation-resistant medical materials.

3. A method for producing a radioprotective product, comprising:
   administering or admixing a polyamino acid or polyamino acids or at least one derivative selected from the group consisting of polyamino acid esters, and copolymers comprising polyamino acids and other polymers (except for polyamino acid compounds in which a residue of aminobenzaldehyde semicarbazone or aminobenzaldehyde thiosemicarbazone is bonded to carboxylic acid at the ω-position of polyglutamic acid or polyaspartic acid), to or with a product in an amount effective to make said product radioprotective.

4. A method for blocking or reducing adverse effects of radiations on an object, the method, comprising contacting the object with a radioprotective material comprising a polyamino acid or polyamino acids or at least one derivative selected from the group consisting of polyamino acid esters, and copolymers comprising polyamino acids and other polymers (except for polyamino acid compounds in which a residue of aminobenzaldehyde semicarbazone or aminobenzaldehyde thiosemicarbazone is bonded to carboxylic acid at the ω-position of polyglutamic acid or polyaspartic acid).

5. A method according to claim 4, wherein the radioprotective material is mixed with, placed over, or immobilized on the object.

6. A method for blocking or reducing adverse effects of radiations on an object, the method comprising contacting the object with the radioprotective product according to claim 1.

7. A method according to claim 6, wherein the radioprotective product is administered to, placed over or applied to the object.

8. A method for production of a radioprotective material, comprising:
   administering or admixing a polyamino acid or polyaminoacids or at least one derivative selected from the group consisting of polyamino acid esters, and copolymers comprising polyamino acids and other polymers, for production of a radioprotective product which provides protection from at least one member selected from the group consisting of cosmic rays, radio waves, electromagnetic waves, infrared radiation, visible light, alpha rays, beta rays, proton beams, baryon beams, X rays, gamma rays, electron beams and neutron beams.

9. A method of producing a radioprotective product comprising using a radioprotective material produced by a method comprising adding a polyamino acid or acids or a derivative or derivatives thereof to a base material, wherein if the radioprotective material is a polyamino acid compound having a residue of aminobenzaldehyde semicarbazone or aminobenzaldehyde thiosemicarbazone, the residue is not bonded to carboxylic acid at the ω-position of polyglutamic acid or polyaspartic acid.

* * * * *